United States Patent [19]
Gross et al.

[11] Patent Number: 5,896,879
[45] Date of Patent: Apr. 27, 1999

[54] FLOW DAMPER FOR A CLEANING STATION

[75] Inventors: Jürgen Gross, Hofheim; Dieter Bickoni, Hochheim; Heinz Neuberger, Selters; Hugo Wilmes, Bad Soden; Helmut Königstein, Pohlheim; Martin Schleicher, Friedrichsdorf, all of Germany

[73] Assignee: Behhring Diagnostics GmbH, Marburg, Germany

[21] Appl. No.: 08/840,635

[22] Filed: Apr. 25, 1997

[30] Foreign Application Priority Data

Apr. 30, 1996 [DE] Germany ............ 196 17 206

[51] Int. Cl.⁶ .................................................. B08B 3/04
[52] U.S. Cl. ................................. 134/182; 73/864.22
[58] Field of Search ........................... 134/154, 170, 134/182, 183; 73/864.22, 864.23, 864.24; 141/90, 91

[56] References Cited

U.S. PATENT DOCUMENTS

| 3,912,535 | 10/1975 | Rauser | 141/90 X |
| 4,076,503 | 2/1978 | Atwood et al. | 141/90 X |
| 4,730,631 | 3/1988 | Schwartz | 134/155 |
| 5,133,373 | 7/1992 | Hoffman et al. | 134/170 X |
| 5,186,194 | 2/1993 | Kitajima | 134/170 X |

FOREIGN PATENT DOCUMENTS

WO 97/03766 2/1997 WIPO ............ B08B 9/02

Primary Examiner—Philip R. Coe
Attorney, Agent, or Firm—Finnegan, Henderson, Farabow, Garrett & Dunner, L.L.P.

[57] ABSTRACT

A flow damper for cleaning stations, in particular for cleaning pipettor tips, is described, a cleaning liquid being introduced into the cleaning station through a pipettor needle and flowing around the pipettor tip before it is conducted away out of the cleaning station. In order to avoid wetting of the isolation surfaces of the pipettor needle and a level detector electrode, if provided, there are provided, according to the invention, in the cleaning station at least one screen having a preferably central entry orifice for the jet of liquid emerging from the pipettor needle and a device for diverting the liquid flow in the direction essentially opposite that of the entering jet of liquid. Furthermore, a plurality of exit orifices, preferably arranged radially around the entry orifice, for the diverted liquid flow are formed in the at least one screen.

23 Claims, 4 Drawing Sheets

FLOW DAMPER FOR A CLEANING STATION

BACKGROUND OF THE INVENTION

1. Field of the Invention

The invention relates to a flow damper for a cleaning station, in particular for cleaning pipette tips, a cleaning liquid being introduced into the cleaning station through a pipette needle, and flowing around the pipette tip before it is conducted away out of the cleaning station, and relates to a cleaning station having such a flow damper.

2. Description of the Related Art

After processing reagents or patient samples, the pipette tips which have come into contact with them must be cleaned before they can be used for processing further reagents or samples. The pipette tips are usually cleaned in overflow cleaning stations with cylindrical overflow vessels in which a cleaning liquid is injected at a high speed through the pipette needle. The cleaning fluid accumulates there and flows around and cleans the pipette needle from the outside before it is conducted away via an overflow. Owing to the high flow speeds required for the internal cleaning of the pipette needle, severe turbulences occur in the overflow vessels, generating waves, bubbles and splashes onto the surface of the vessel. As a result, the upper isolation surfaces of the pipette needle which do not have to be cleaned and of a level detector electrode used to determine the position of the pipette needle in the cleaning station, also used at other processing stations, are also covered with liquid. Apart from the fact that this covering with liquid may lead to a carry-over of reagents or patient samples, the liquid adhering to the isolation surfaces of the pipette needle and the level detector electrode adversely affects the level detection based on a potential measurement, in that it generates a short circuit which makes reliable position measurement impossible.

SUMMARY OF THE INVENTION

The object of the invention is therefore to avoid such problems of level detection and carry-over in cleaning stations for cleaning pipette tips.

This object is achieved by the invention essentially in that there are provided in the cleaning station at least one screen having a preferably central entry orifice for the jet of liquid emerging from the pipette needle and a device for diverting the liquid flow in the direction essentially opposite that of the entering jet of liquid, and in that a plurality of exit orifices, preferably arranged radially around the entry orifice, for the diverted liquid flow are formed in the at least one screen.

By means of the diversion of the liquid flow and the screen provided, through which the liquid flow must pass, a substantial calming of the flow is achieved, thus avoiding wetting of the isolation surfaces of the pipette needle and the level detector electrode.

In a preferred embodiment of the invention, further increased flow damping is achieved in that two screens are arranged one above the other, forming a flow space between them.

In this case, the exit orifices of the two screens are preferably arranged in each case azimuthally offset relative to one another so that the liquid cannot flow straight through the two screens, but is calmed to an even greater extent by the additional diversion.

The risk of the level detector electrode being covered with cleaning liquid can be further reduced by the fact that at least the upper screen has no exit orifice in one circumferential area (assigned to the level detector electrode). Consequently, no liquid passes through the upper screen in the region of the level detector electrode so that waves, bubbles and splashes only form here to a minimal extent, if at all.

In order to permit unobstructed outflow of the liquid through the exit orifices, provision is made according to the invention for the sum of the areas of the radially distributed exit orifices of a screen to be larger than the area of the entry orifice of said screen.

In a further embodiment of the invention, the diversion of the jet of liquid introduced through the entry orifice of the screens is effected by the fact that a cone or the like pointing toward the entry orifice is provided below the entry orifice of the bottom screen, over which cone the entering jet of liquid is diverted radially outward. The liquid flow is then diverted further along the walls of the flow damper so that it can flow off upward through the exit orifices in the screens.

In order to be able to feed the liquid flow flowing off to an overflow path in a targeted manner, the invention provides raised side walls adjoining an overflow edge for the liquid running off.

Simple manufacture and the possibility of retrofitting, even of existing cleaning stations, can be achieved by the invention due to the fact that the flow damper is designed as an insert comprising a plurality of individual elements, in particular made of plastic, which are connected to one another, for example, by means of a plug-in or bonded connection.

Additionally, the flow damper is preferably inserted into a corresponding recess in the cleaning station.

According to the invention, a defined flow of the cleaning liquid is achieved in that the flow damper is sealed off relative to the recess.

A further embodiment provides improved of the runoff behavior of the cleaning liquid and is achieved by improved shaping of an overflow path to receive the liquid flowing off out of the flow damper. In this case, the overflow edge of the flow damper can be arranged flush with an overflow edge of the recess in the cleaning station or lie slightly below the overflow edge of the recess. In contrast to the cleaning stations previously used, in which a cylindrical tube insert was inserted into the cleaning station and, at the beginning of each cleaning process, an upwardly curved mass of liquid was formed which was only removed, after overcoming the surface tension, by running off along the oblique surface in the second part of the cleaning process, the overcurvature of liquid at the beginning of the cleaning process can be evened out by lowering the insert below the overflow edge of the recess in the cleaning station and making an overflow path in the cleaning station, so that a stable level is set throughout the entire cleaning process. This also contributes toward preventing wetting of the isolation surfaces of the level detection.

Further developments, advantages and possible applications of the invention also emerge from the following description of an exemplary embodiment and from the drawing. In this case, all the features described and/or illustrated form, by themselves or in any desired combination, the subject-matter of the invention, irrespective of their composition in the claims or of their reference.

DESCRIPTION OF THE PREFERRED EMBODIMENTS

Figure 1:
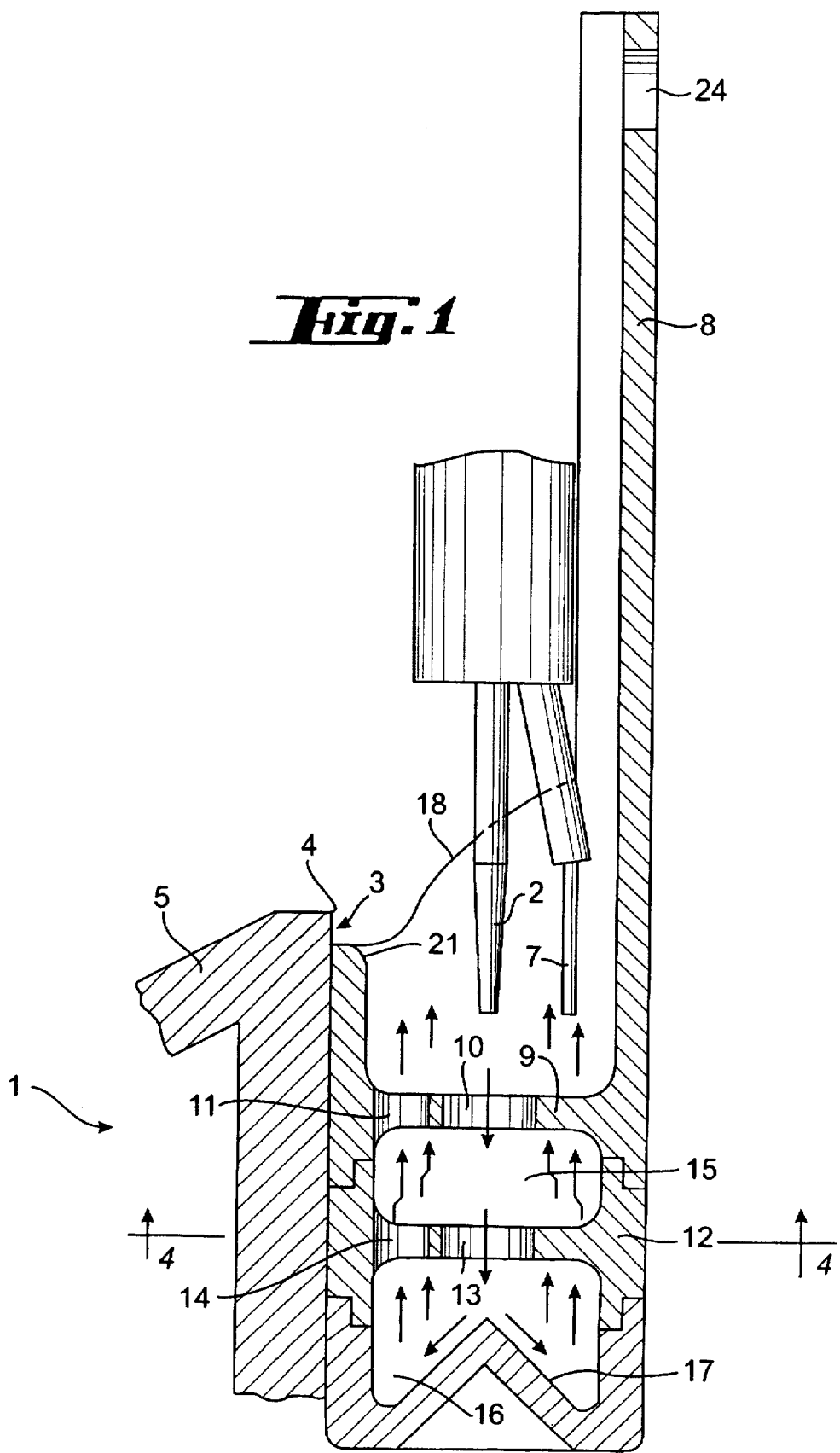
FIG. 1 is a sectional view of a flow damper according to the invention with an indicated pipette needle and overflow edge of the cleaning station.
Figure 2:
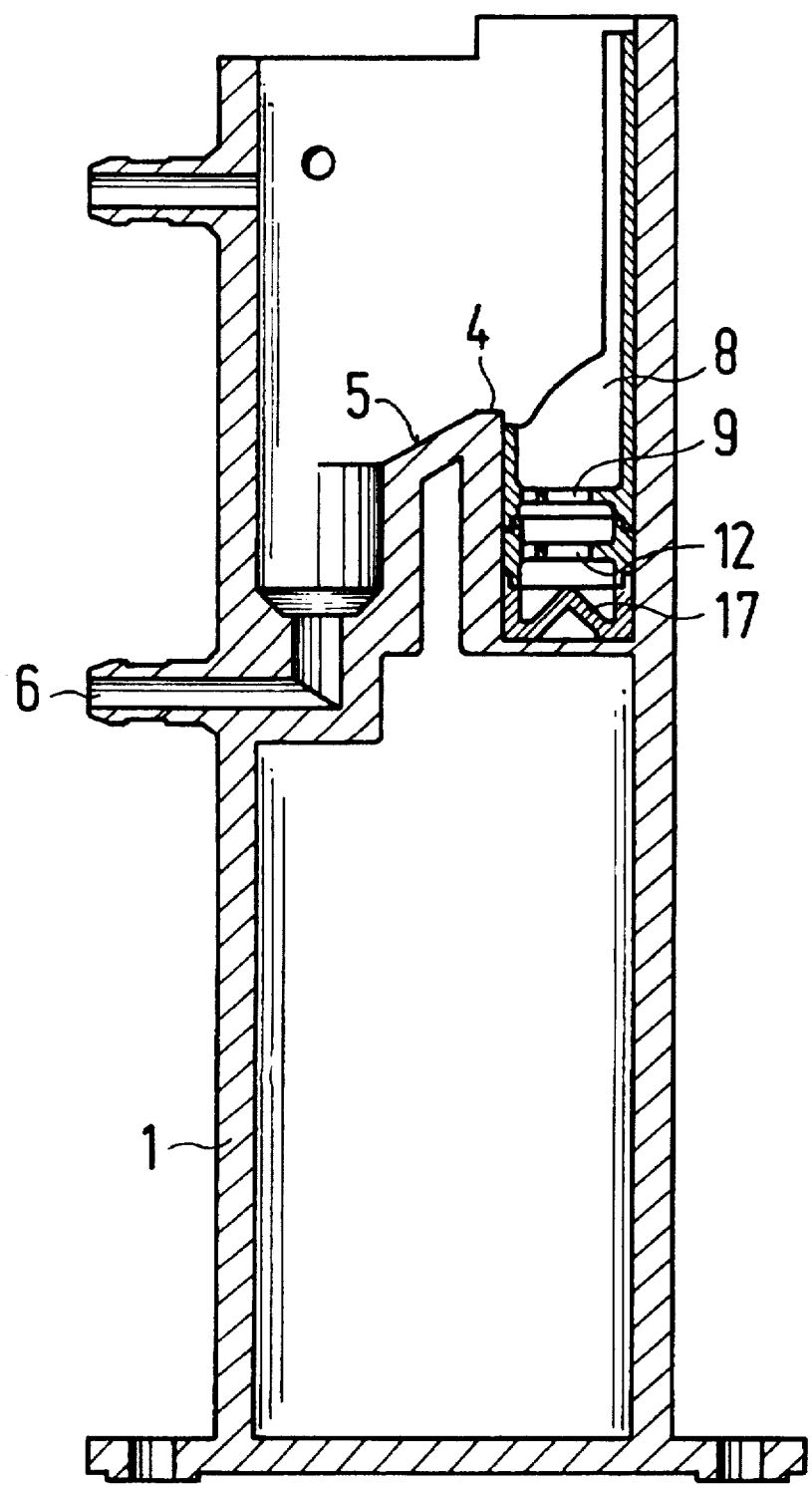
FIG. 2 is a sectional view of a cleaning station with an inserted flow damper.

A cleaning station 1 illustrated in FIGS. 1 and 2 is used for cleaning pipette needles 2 by injecting a cleaning agent at a high flow speed through the pipette needle 2 into a recess 3 formed in the cleaning station 1. The cleaning liquid collects in the recess 3 and flushes the pipette needle 2 from the outside before it is fed via an overflow edge 4 and an overflow path 5 to a runoff 6.

The correct positioning of the pipette needle 2 in the cleaning station 1 is controlled by means of a level detector electrode 7 which, by means of a potential measurement, detects the entry of the pipette needle 2 into the cleaning liquid and passes information of such entry on, for example to an electronic control. The level detector electrode 7 is also used for positioning the pipette needle in subsequent stations. In order to be able to accurately detect the entry of the pipette needle 2 into the liquid, it must be ensured that there is no conductive liquid on the isolation surfaces in the upper region of the pipette needle 2 or on the level detector electrode 7, which would lead to a short circuit and thus prevent unambiguous measurement.

In order to prevent strong turbulence waves, and bubbles from forming on the surface when the cleaning liquid is injected, resulting in the isolation surfaces of the pipette needle 2 and of the level detector electrode 7 being covered with conductive cleaning liquid, a flow damper 8 is inserted into the recess 3 in the cleaning station 1.

Figure 3:
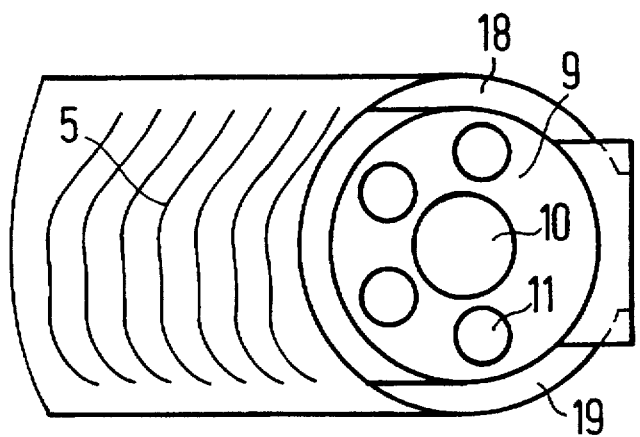
FIG. 3 is a cross sectional view of the illustration according to FIG. 1 without a pipette needle.
Figure 4:
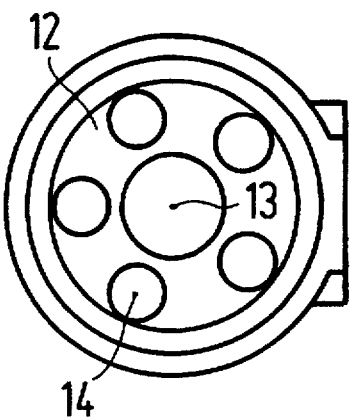
FIG. 4 shows a plan view of a middle section of the flow damper taken along line 4—4.

The flow damper 8 has an upper screen 9 having a central entry orifice 10 and exit orifices 11, arranged radially around the entry orifice 10, and a second screen 12 arranged below upper screen 9, likewise having a central entry orifice 13 and exit orifices 14 arranged radially around entry orifice 13. A first flow space 15 is provided between the screens 9, 12. Provided below the second screen 12 is a second flow space 16 which is bounded at the bottom by a cone 17 arranged coaxially with the entry orifices 10, 13 and pointing upward. As shown in FIGS. 3 and 4, the exit orifices 11, 14 of the first and second screens 9, 12 are offset azimuthally relative to one another such that they are not aligned with one another. Furthermore, no exit orifice 11 is provided in the first screen 9 in the area located below the level detector electrode 7. The area of the exit orifices 11, 14 of at least one screen 9, 12 is larger than the area of the entry orifice 10, 13 of such screen 9, 12.

When the cleaning liquid is injected through the nozzle of small cross section of the pipette needle 2, the cleaning liquid is fed at a high speed (for example 1.6 ml/s) into the entry orifice 10 of the upper screen 9 and further through the first flow space 15 and the entry orifice 13 of the second screen 12 into the second flow space 16 until it impinges on the cone 17 and is diverted outward by the latter. The liquid is diverted upward along the side walls of the flow damper 8 where it is conducted upward through the exit orifices 14 of the second screen into the first flow space 15 and through the exit orifices 11 of the first screen 9. In FIG. 1, the flow path of the cleaning liquid is indicated by arrows. Turbulences are damped by the substantial diversion of the flow of cleaning liquid and by the screens 9, 12, such that no significant waves and bubbles form on the surface which could lead to wetting of the isolation surfaces of the pipette needle 2 and of the level detector electrode 7. A further diversion of the flow of cleaning liquid is brought about by the azimuthal offset of the exit orifices 11, 14 of screens 9 and 12 respectively, leading to additional calming.

The cleaning liquid flows out of the flow damper 8 via the overflow edge 4 and the overflow path 5 into the runoff 6 of the cleaning station 1. By means of raised side walls 18, 19 of the flow damper 8, the cleaning liquid is fed in a targeted manner to the overflow path 5 which, due to adapted shaping, ensures further calming and stabilizing of the liquid level.

Figure 5:
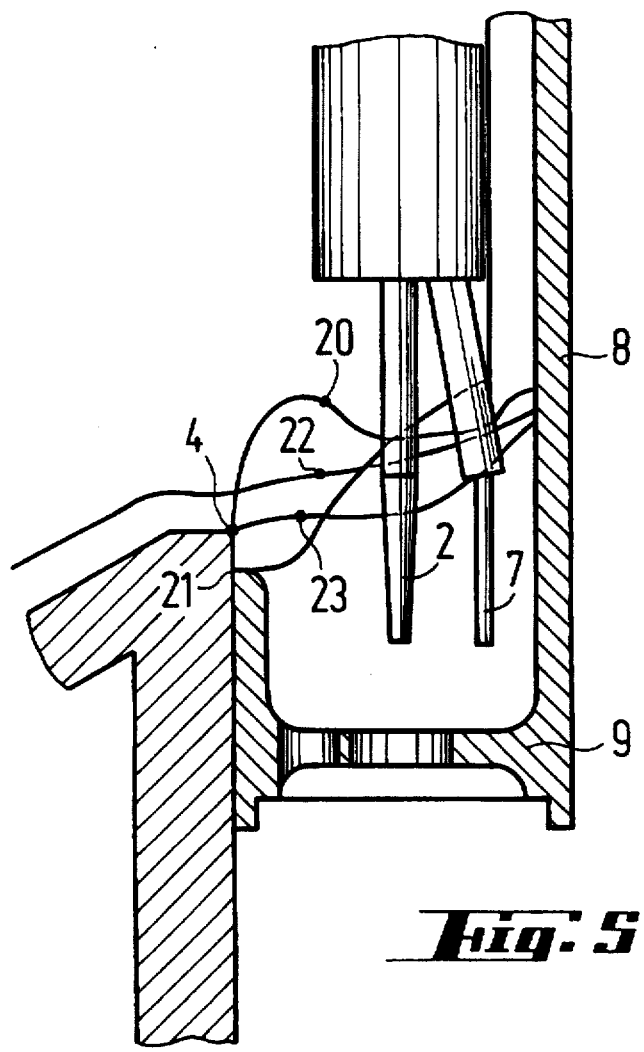
FIG. 5 is a comparative illustration of a sectional view of a cleaning station comparing the liquid level developing in the prior art and in the present invention.

FIG. 5 illustrates the liquid levels developing during the cleaning operation. In this case, serving as a comparison line, 20 denotes an upwardly curved mass of liquid, such as occurred in the cylindrical tube inserts of the prior art and previously used without a flow damper at the beginning of each cleaning process. This mass of liquid 20 was only removed after overcoming the surface tension by runoff over the overflow path in the second part of the cleaning process. In this case too, the isolation surfaces of the level detection were at risk.

Figure 6:
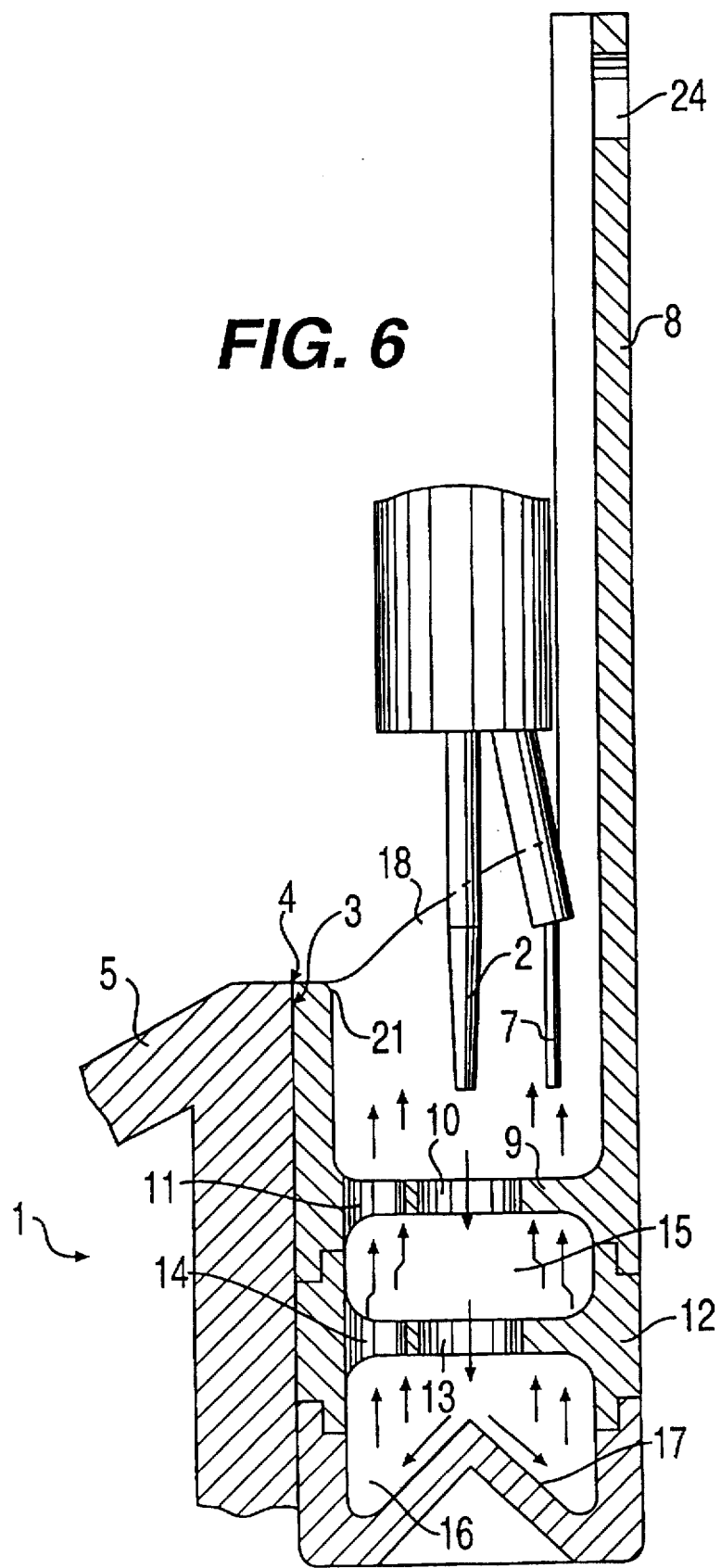
FIG. 6 is a cross-sectional view according to another embodiment of the present invention with a cleaning station having an inserted flow damper where the overflow edge of the cleaning station is flush with the overflow edge of the flow damper.

In the embodiment of the present invention illustrated, the flow damper 8 is inserted into the recess 3 in the cleaning station 1 to the extent that an overflow edge 21 of the flow damper 8 lies just below the overflow edge 4 of the recess 3. As a result, the overcurvature of the liquid at the beginning of the cleaning process can be evened out so that a stable level denoted by line 22 develops throughout the entire cleaning process. On completion of the cleaning operation, a reproducible level denoted by line 23 develops which terminates with the overflow edge 4 of the recess 3. Alternatively, as shown in FIG. 6, provision may also be made for the overflow edge 21 of the flow damper 8 to terminate flush with the overflow edge 4 of the recess 3, in which case, however, there is a risk of a slight mass of liguid, similar to the mass of liquid 20 occurring in the prior art. The flow damper 8 is composed of three individual elements 9, 12, 17 which are made of plastic by a suitable method, for example by injection molding, and are connected to one another by means of a plug-in or bonded connection. The flow damper 8 is designed as an insert which can be inserted as a whole into a corresponding recess 3 in the cleaning station 1 and can easily be exchanged with the aid of a hole 24 formed in the upper section of the flow damper 8. In this way, it is possible to retrofit cleaning stations 1, even those which are already in use, with the flow damper 8 according to the invention and to avoid the level detection errors occurring in those cleaning stations.

As has been established in trials, a significant calming of the liquid level 22 dropping slightly toward the overflow edge 4 can be detected with use of the flow damper 8 the present invention. Wetting of the pipette needle 2 and the level detector electrode 7 in the upper isolation region and the disturbance of the level detection this entails were no longer observed.

What is claimed is:

1. A flow damper for a cleaning station where cleaning liquid is introduced through a pipette needle and flows around the pipette needle for cleaning pipette tips before the cleaning liquid is conducted away from the cleaning station, the flow damper comprising:

at least one screen having a entry orifice for receiving the cleaning fluid from the pipette needle;

means for diverting the flow of cleaning liquid in a direction essentially opposite to the direction in which it was introduced; and a plurality of exit orifices formed in the at least one screen for receiving the diverted liquid flow.

2. The flow damper of claim 1, wherein the entry orifice is located in the center of the screen and the plurality of exit orifices are arranged radially around the entry orifice.

3. The flow damper of claim 1, including upper and lower screens forming a flow space between them.

4. The flow damper of claim 3, wherein each of the upper and lower screens includes a plurality of exit orifices, and the exit orifices of the upper screen are azimuthally offset relative to the exit orifices of the lower screen.

5. The flow damper of claim 3, wherein a circumferential region of the upper screen contains no exit orifices.

6. The flow damper of claim 3, wherein the sum of the areas of the exit orifices of each screen is greater than the area of the entry orifice of that screen.

7. The flow damper of claim 3, wherein the means for diverting the liquid flow is a cone having a base and a point, wherein the cone is located below the lower screen with its point facing toward the entry orifice of the lower screen.

8. The flow damper of claim 3, wherein the flow damper further includes raised side walls, the side walls adjoining an overflow edge of the cleaning station when the flow damper is inserted within the cleaning station.

9. The flow damper of claim 3, wherein the flow damper is an insert sized to fit into the cleaning station, and the flow damper comprises a plurality of plastic elements connected to one another.

10. The flow damper of claim 9, wherein the elements are connected by either snap-fitting or bonding.

11. The flow damper of claim 1, wherein a circumferential region of the upper screen contains no exit orifices.

12. The flow damper of claim 1, wherein the sum of the areas of the exit orifices is greater than the area of the entry orifice.

13. The flow damper of claim 1, wherein the flow damper further includes raised side walls, the side walls adjoining an overflow edge of the cleaning station when the flow damper is inserted within the cleaning station.

14. The flow damper of claim 1, wherein the flow damper is an insert sized to fit into the cleaning station, and the flow damper comprises a plurality of plastic elements connected to one another.

15. The flow damper of claim 14, wherein the elements are connected by either snap-fitting or bonding.

16. A cleaning station for cleaning pipette tips, wherein a cleaning fluid is introduced through a pipette needle a flows around the pipette needle to clean pipette tips before being conducted out of the cleaning station, the cleaning station comprising:

a flow damper formed as an insert and sized to fit into the cleaning station, the flow damper comprising:

at least one screen having a entry orifice for receiving the cleaning fluid from the pipette needle;

means for diverting the flow of cleaning liquid in a direction essentially opposite to the direction in which it was introduced; and a plurality of exit orifices formed in the at least one screen for receiving the diverted liquid flow.

17. The cleaning station of claim 16, wherein the entry orifice is located in the center of the screen and the plurality of exit orifices are arranged radially around the entry orifice.

18. The cleaning station of claim 16, wherein the flow damper includes upper and lower screens forming a flow space between them.

19. The cleaning station of claim 16, wherein the cleaning station further comprises a recess sized to receive the flow damper.

20. The cleaning station of claim 19, wherein the flow damper is sealed off relative to the recess.

21. The cleaning station of claim 19, wherein the flow damper further includes an overflow edge sized to terminate flush with an overflow edge of the recess of the cleaning station when the flow damper is inserted within the cleaning station.

22. The cleaning station of claim 19, wherein the flow damper further includes an overflow edge, and the recess of the cleaning station includes an overflow edge, wherein the overflow edge of the recess of the cleaning station lies slightly higher than the overflow edge of the flow damper when the flow damper is inserted within the cleaning station.

23. The cleaning station of claim 16 further including an overflow path for receiving cleaning liquid flowing out of the flow damper.

* * * * *

UNITED STATES PATENT AND TRADEMARK OFFICE
CERTIFICATE OF CORRECTION

PATENT NO. : 5,896,879
DATED : April 27, 1999
INVENTOR(S) : Jürgen GROß, et al.

It is certified that error appears in the above-identified patent and that said Letters Patent is hereby corrected as shown below:

Claim 1, column 5, line 7, "a entry" should read --an entry--.

Claim 16, column 6, line 10, "a flows" should read --and flows--.

Claim 16, column 6, line 16, "a entry" should read --an entry--.

Signed and Sealed this

Eighteenth Day of January, 2000

Attest:

Q. TODD DICKINSON

*Attesting Officer*     *Commissioner of Patents and Trademarks*